(12) United States Patent
Haggblom et al.

(10) Patent No.: US 10,046,129 B2
(45) Date of Patent: Aug. 14, 2018

(54) SYSTEM AND METHOD FOR VENTILATING LUNGS

(71) Applicant: GENERAL ELECTRIC COMPANY, Schenectady, NY (US)

(72) Inventors: Tom Jakob Haggblom, Vantaa (FI); Erkki Paavo Heinonen, Helsinki (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 212 days.

(21) Appl. No.: 15/171,798

(22) Filed: Jun. 2, 2016

(65) Prior Publication Data

US 2016/0354568 A1    Dec. 8, 2016

Related U.S. Application Data

(63) Continuation of application No. 13/074,601, filed on Mar. 29, 2011.

(30) Foreign Application Priority Data

Mar. 29, 2010  (EP) ..................... 10158134

(51) Int. Cl.
*A61M 16/20* (2006.01)
*A61M 16/00* (2006.01)
(Continued)

(52) U.S. Cl.
CPC ........ *A61M 16/0078* (2013.01); *A61M 16/00* (2013.01); *A61M 16/0081* (2014.02); *A61M 16/024* (2017.08); *A61M 16/12* (2013.01); *A61M 16/204* (2014.02); *A61M 16/205* (2014.02); *A61M 16/107* (2014.02); *A61M 16/22* (2013.01); *A61M 2016/0015* (2013.01); *A61M 2016/0021* (2013.01);
(Continued)

(58) Field of Classification Search
CPC .......... A61M 16/0078; A61M 16/0075; A61M 16/20; A61M 16/08; A61M 2205/50; A61M 16/201
USPC ............ 128/205.13–205.14, 205.17, 204.21, 128/204.23, 200.24, 203.12–203.15, 128/203.24–203.25, 203.28, 204.28, 128/205.11
See application file for complete search history.

(56) References Cited

U.S. PATENT DOCUMENTS 3,200,816 A * 8/1965 Bartlett, Jr. ........... A61M 16/00
                                                        128/204.21
3,901,230 A * 8/1975 Henkin ............... A61M 16/104
                                                        128/205.15
(Continued)

*Primary Examiner* — Andrew S Lo

(57) ABSTRACT

A system for ventilating lungs of a subject is disclosed herein. The system includes a control unit configured to control operation of the system. The system also includes a machine ventilator circuit configured to assist the breathing functions of the subject, the machine ventilator circuit includes an inspiration delivery unit, and an expiration circuit. The system also includes a manual ventilation circuit comprising a manual bag guiding a gas from the manual bag wherein a gas flow is guided out from the manual bag to assist an inspiration phase, a gas flow is received to fill the manual bag during an expiration phase, and wherein the gas flow received to fill the manual bag during the expiration phase at least partially comprises the gas flow guided to assist the inspiration phase.

16 Claims, 3 Drawing Sheets

(51) Int. Cl.
  *A61M 16/12* (2006.01)
  *A61M 16/10* (2006.01)
  *A61M 16/22* (2006.01)

(52) U.S. Cl.
  CPC .............. *A61M 2016/0027* (2013.01); *A61M 2016/0042* (2013.01); *A61M 2205/502* (2013.01)

(56) References Cited

U.S. PATENT DOCUMENTS

| | | | | |
|---|---|---|---|---|
| 3,903,881 A * | 9/1975 | Weigl | .................. | A61M 16/206 128/204.25 |
| 4,883,051 A * | 11/1989 | Westenskow | ......... | A61M 16/00 128/204.21 |
| 4,972,842 A * | 11/1990 | Korten | .................. | A61B 5/087 128/200.24 |
| 5,373,842 A * | 12/1994 | Olsson | .................. | A61M 16/00 128/204.21 |
| 5,497,767 A * | 3/1996 | Olsson | .................. | A61M 16/00 128/205.13 |
| 5,678,540 A * | 10/1997 | Kock | .................... | A61M 16/00 128/205.13 |
| 5,694,924 A * | 12/1997 | Cewers | ................ | A61M 16/01 128/204.21 |
| 5,875,777 A * | 3/1999 | Eriksson | ............. | A61M 16/024 128/204.21 |
| 8,857,429 B2 * | 10/2014 | Spandorfer | ......... | A61M 15/009 128/200.23 |
| 2001/0029946 A1 * | 10/2001 | Kitten | ................... | A61M 16/01 128/203.14 |
| 2002/0104538 A1 * | 8/2002 | Emtell | .............. | A61M 16/0078 128/205.14 |
| 2004/0144385 A1 * | 7/2004 | Bromster | ............. | A61M 16/08 128/205.13 |
| 2007/0044798 A1 * | 3/2007 | Levi | ...................... | A61M 16/00 128/204.23 |
| 2007/0125377 A1 * | 6/2007 | Heinonen | ............. | A61M 16/01 128/204.21 |
| 2008/0202520 A1 * | 8/2008 | Mitton | ................ | A61M 16/024 128/204.21 |
| 2008/0230064 A1 * | 9/2008 | Tham | ................... | A61M 16/024 128/204.23 |
| 2009/0250059 A1 * | 10/2009 | Allum | ............... | A61M 16/0051 128/204.26 |
| 2009/0277448 A1 * | 11/2009 | Ahlmen | ............... | A61M 16/024 128/204.21 |
| 2010/0252046 A1 * | 10/2010 | Dahlstrom | ............ | A61M 16/01 128/205.24 |
| 2011/0214673 A1 * | 9/2011 | Masionis | .......... | A61M 16/0078 128/205.13 |
| 2012/0174925 A1 * | 7/2012 | Tham | ................ | A61M 16/0051 128/204.21 |
| 2014/0060539 A1 * | 3/2014 | Korten | ............. | A61M 16/0051 128/204.23 |

* cited by examiner

SYSTEM AND METHOD FOR VENTILATING LUNGS

CROSS REFERENCE TO RELATED APPLICATION

This application is continuation of U.S. application Ser. No. 13/074,601, filed Mar. 29, 2011, which application was published on Sep. 29, 2011, as U.S. Publication No. US20110232641, which claims priority to EP Application No. 10158134.6, filed Mar. 29, 2010, published on Oct. 5, 2011 as EP Publication No. EP2371410, the applications of which are incorporated herein by reference in their entirety.

BACKGROUND OF THE INVENTION

This disclosure relates generally to an apparatus and method for ventilating lungs of a subject enabling to choose one of a machine ventilation for assisting breathing functions and a manual ventilation with a manual bag which can be compressed for an inspiration.

Presently, anesthesia machines are optimized for delivering anesthesia to a patient using volatile anesthetic agent liquids. In such systems, the anesthetic agent is vaporized and mixed into the breathing gas stream in a controlled manner to provide a gas mixture for anesthetizing the patient for a surgical operation. The most common volatile anesthetic agents are halogenated hydrocarbon chains, such as halothane, enflurane, isoflurane, sevoflurane, and desflurane. Additionally, nitrous oxide ($N_2O$) can be counted in this group of volatile anesthetic agents, although the high vapor pressure of nitrous oxide causes nitrous oxide to vaporize spontaneously in the high pressure gas cylinder, where it can be directly mixed with oxygen. The anesthetizing potency of nitrous oxide is seldom enough to anesthetize a patient and therefore is typically mixed with another volatile agent.

Since volatile anesthetic agents are expensive and environmentally damaging to the atmospheric ozone layer, anesthesia machines have been developed to minimize the use of these gases. To keep patient's anesthetized, a defined brain partial pressure for the anesthetic agent is required. This partial pressure is maintained by keeping the anesthetic agent partial pressure in the lungs adequate. During a steady state, the lung and body partial pressures are equal, and no net exchange of the anesthetic agent occurs between the blood and the lungs. However, to provide oxygen and eliminate carbon dioxide, continuous lung ventilation is required.

Anesthesia machines designed to deliver volatile anesthetic agents are designed to provide oxygen to the patient and eliminate carbon dioxide, while preserving the anesthetic gases. These goals are typically met using a re-breathing circuit, where an exhaled gas is reintroduced into the inhalation limb leading to the patient. In such a re-breathing circuit, carbon dioxide is absorbed from the expired gases by a carbon dioxide absorber. Before inhalation by the patient, the inhalation gas is supplied with additional oxygen and vaporized in aesthetic agents based upon the patient demand. In this arrangement, the additional gas flow added to the re-breathing circuit can be less than 0.5 L/min although the patient ventilation may be 5-10 L/min. The positive pressure inspiration is typically carried out using a ventilator, which is typically gas driven. In these ventilators, the patient breathing gas is pressurized by controlling a ventilator drive gas flow through a separate system maintaining the breathing gas separate from the ventilator drive gas. Such gas separation system may have form of a long reciprocating gas column or a physical flexible barrier construction.

Intravenously administered drugs provide an alternative to the volatile anesthetic agents. When an intravenous anesthesia is utilized, the primary functionality of the anesthesia re-breathing circuit is no longer needed, since the vaporized anesthetic agent is no longer circulating with the breathing gases. When intravenously administered anesthetic drugs are utilized, the anesthesia machine may use an open breathing circuit where a mixture of fresh oxygen and nitrogen is provided at the rate required by the patient and the expired gases can be removed from the circulation. In such an open system, carbon dioxide absorption is no longer needed since the re-circulation has been eliminated. Further, the isolation between the patient gases and the drive gases are no longer needed when the ventilation gases are provided directly to the patient. Thus, an anesthesia ventilator optimized for the intravenous anesthesia does not need the gas separation system and the carbon dioxide absorber. Further, a vaporizer for the volatile anesthetic agents is also no longer needed. These simplifications provide advantages in equipment size, eliminate much of the cleaning requirements by reducing the number of contaminated components, and streamlines the anesthesia machine manufacturing process.

Independently of the anesthesia practice, anesthesia ventilation involves ability for the clinician to manually ventilate the patient. This functionality is typically utilized during an anesthesia induction, weaning the patient from the anesthesia and ventilator, in assistance of spontaneous breathing and for the lung recruitment.

A desired property of manual ventilation system is given haptic feedback of the patient breath volume. Such feedback is achieved when the patient exhalation volume is collected to the manual bag, which is done in the following state of the art solutions.

The currently most used arrangement in ventilating manually is to have a breathing system equipped with an APL (Airway Pressure Limiting) valve. When using an airway pressure limiting valve the operating principle is that the valve is set to an pre-determined setting and when the manual ventilation bag is squeezed the gas volume is initially delivered to the patient, but when the APL pressure limit is reached the valve starts to bleed gas out from the breathing system. The valve will form a resistance and as the bag is further squeezed some of the volume will go to the patient and some will bleed through the valve. The volume going to the patient, if any, is not possible to determine haptically by how much the bag is squeezed. Neither the patient flow resistance can be identified since that is parallel to the APL valve bleeding resistance. If the patient is not ventilated by squeezing the bag, fresh gas or ventilator bias flow will increase the pressure to the APL limit leading to a sustained pressure and possible barotrauma or volutrauma. It is not possible to deliver a PEEP (Positive End Expiratory Pressure) to the patient with the APL valve.

Further development of mechanical manual ventilation valves has been done. An example of such valve is the "Berner valve". This valve controls the breathing circuit and patient pressure at on low level during expiration and closes the valve during inspiration. The switchover between the phases is triggered with gas impulses caused by squeezing and releasing of the manual bag. To ventilate using this valve, both the bag compression and release actions need to be rigorous enough to generate the required impulse. Yielding from this, the Berner valve involves a safety problem related to every manual breath: Would the sensing of expiration fail, the valve remains closed resulting to unlimited breathing circuit and patient pressure increase. This problem related to the difficult use of the method, which has limited its clinical use.

The explained solutions represent a separate pressure control during the manual ventilation and mechanical ventilation most often controlled electronically using another pressure control valve. Also a solution using the same pressure control valve in both ventilation modalities is known. Because of the electrical breathing circuit and patient pressure control, the control algorithm can follow either the "APL" or "Berner" principle. Ability to set a maximum pressure limit solves the disadvantage of the "Berner" method. Also the minimum pressure during expiration (PEEP) can be controlled according to clinical demand.

For identification of the breathing phase, a predetermined control rule can be used. The controller of this system compares the measured breathing circuit pressure and/or breathing circuit flow pattern with the predetermined control rule, and based on this comparison, determines whether the manual breath cycle is inspiration or expiration: Compression of the manual bag increases the breathing circuit pressure and causes gas flow in the breathing circuit towards the patient. Respectively, release of the manual bag causes breathing circuit pressure decrease and breathing circuit flow from the patient towards the manual bag Problem of the described system is that at the time the manual bag compression is started, the breathing circuit pressure control valve is open, and the compression necessarily does not yield to the breathing circuit pressure and/or flow pattern expected from the predetermined control rule. Therefore, even here the initial compression must be strong enough to cause the expected changes despite of the adjacent open pressure control valve.

BRIEF DESCRIPTION OF THE INVENTION

The above-mentioned shortcomings, disadvantages and problems are addressed herein which will be understood by reading and understanding the following specification.

In an embodiment, an arrangement for ventilating lungs of a subject includes a machine ventilator circuit for assisting breathing functions and which circuit includes an inspiration delivery unit for delivering a gas flow to assist an inspiration and an expiration circuit for controlling a discharge of an expiration gas. The arrangement for ventilating lungs of a subject also includes a manual ventilation circuit for enabling the manual ventilation to assist breathing functions, said manual ventilation circuit comprising a manual bag to assist the inspiration and to receive a gas flow for filling the manual bag during the expiration. The arrangement for ventilating lungs of a subject further includes a control unit for controlling an operation of the arrangement. The manual bag is filled during the expiration at least partly by the gas used to assist the inspiration. The manual ventilation circuit also includes a sensor to detect a flow direction inside the manual ventilation circuit and to produce for the control unit a signal to determine the flow direction to guide the expiration circuit.

In another embodiment, a method for ventilating lungs of a subject enabling to choose one of a machine ventilation for assisting breathing function and a manual ventilation with a manual bag which can be compressed for an inspiration, the manual ventilation includes providing a gas flow to assist an inspiration by compressing a manual bag increasing a pressure necessary for the inspiration and releasing the manual bag for an expiration. The method for ventilating lungs of a subject in the manual ventilation also includes allowing an extra gas volume to be discharged during the expiration in order to reach a desired level of an expiratory pressure and to be discharged during the inspiration in order to limit an inspiratory pressure to a desired level. The method for ventilating lungs of a subject in the manual ventilation also includes allowing the manual bag to be filled during the expiration at least partly by the gas flow used to assist the inspiration and detecting whether the flow direction is to the manual bag or out from the manual bag. The method for ventilating lungs of a subject in the manual ventilation further includes producing a signal based on detecting and receiving the signal and determining from the signal the flow direction to guide a discharge of the extra gas volume.

In yet another embodiment the method for ventilating under a control of a control unit lungs of a subject enabling to choose one of a machine ventilation method for assisting breathing functions using a machine ventilator circuit and a manual ventilation method using a manual ventilation circuit, the manual ventilation circuit being in flow connection with at least a part of the machine ventilator circuit for making a flow pneumatic contact with the lungs of the subject when the manual ventilation method is chosen and the manual ventilation circuit being in flow connection with an expiration circuit for achieving a desired pressure level under the control of the control unit, the manual ventilation method includes providing a drive gas flow to assist an inspiration by compressing a manual bag of the manual ventilation circuit allowing the pressure increase necessary for the inspiration within the manual ventilator circuit and within the part of the machine ventilator circuit in flow connection with manual ventilator circuit. The method for ventilating under a control of a control unit lungs of a subject in the manual ventilation method also includes releasing the manual bag for an expiration, allowing the manual bag to be filled due to the expiration gas flow and allowing an extra gas volume to be discharged through the expiration circuit during the expiration in order to reach a desired level of end expiratory pressure and during the inspiration in order to limit an inspiratory pressure to a desired level. The method for ventilating under a control of a control unit lungs of a subject in the manual ventilation method further includes detecting the flow direction inside the manual ventilation circuit by means of a sensor, producing a signal based on detecting for the control unit, receiving the signal and determining from the signal the flow direction to guide a discharge of the extra gas volume.

Various other features, objects, and advantages of the invention will be made apparent to those skilled in art from the accompanying drawings and detailed description thereof.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

The embodiments are directed to an arrangement and a method for a use in an intensified breathing, and for a use whenever anesthesia is being delivered to a subject.

Figure 1:
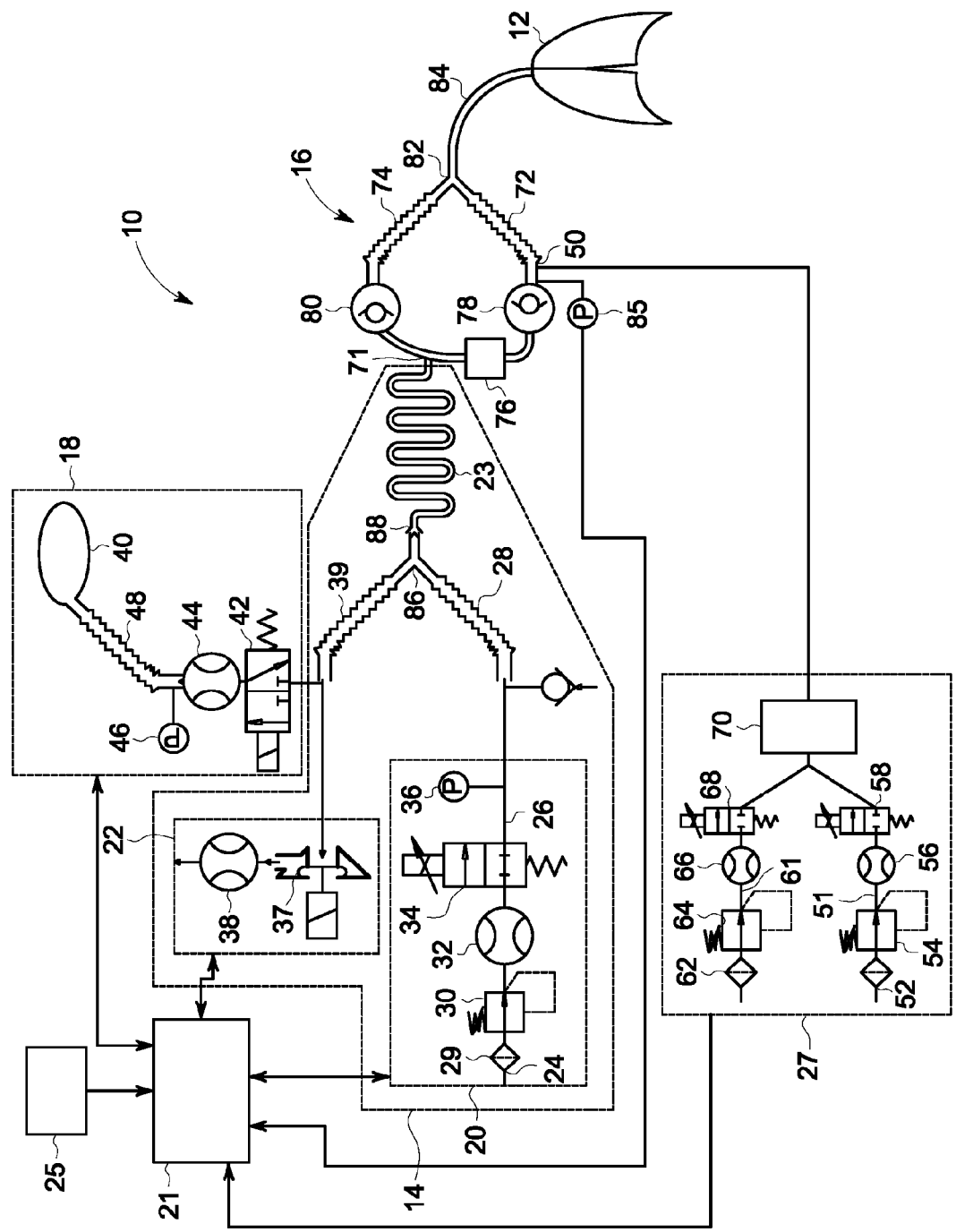
FIG. 1 illustrates an operational diagram of an arrangement for providing an inspiration gas to a subject.

The arrangement 10 for providing an inspiration gas to the subject 12 utilizing a re-breathing system is shown in FIG. 1. The arrangement 10 comprises a machine ventilator circuit 14 for assisting breathing functions of the subject, a breathing circuit 16 for connecting lungs of the subject and the machine ventilator circuit 14 to exchange the gas in the lungs, a manual ventilation circuit 18 for enabling the manual ventilation of the subject and a control unit 21 for controlling an operation of the arrangement 10. The manual ventilation circuit 18 and the machine ventilator circuit 14 can be alternatively selected by an operator. The manual ventilation circuit can be in a gas flow connection with at least a part of the machine ventilator circuit for making a pneumatic contact with the lungs of the subject when the manual ventilation method is chosen. The arrangement 10 shown in FIG. 1 may also comprise a user interface 25 for entering any information needed while ventilating the subject and a gas mixer 27 for supplying a fresh gas for the subject breathing.

The machine ventilator circuit 14 generally comprises an inspiration delivery unit 20 for delivering the gas such as drive gas needed to enable an inspiration of the subject, an expiration circuit 22 for controlling a discharge of the expiration gas and a reciprocating unit 23 such as a well-known bellows and bottle combination, where the bellows are arranged within the bottle, or a long gas flow channel as shown in FIG. 1 for compressing the gas under a control of the drive gas pressure towards lungs of the subject to facilitate the inspiration. Both the inspiration delivery unit 20 and the expiration circuit 22 are controlled by the control unit 21.

As illustrated in FIG. 1, the inspiration delivery unit 20 comprises a compressed gas interface 24 connected to a compressed gas supply (not shown). The compressed gas can be either oxygen or air. Also a mechanism selecting the other if one gets de-pressurized can be applied (not shown). The inspiration delivery unit 20 comprises also a filter 29 for filtering impurities, a pressure regulator 30 for regulating a pressure of gases flowing from the gas interface, a flow sensor 32 for measuring a inspiration delivery flow from the gas interface and a flow control valve 34 for opening or closing the inspiration delivery flow. The flow sensor 32 and flow control valve 34 are each coupled to the control unit 21 to control the inspiration delivery to the subject 12. Further the inspiration delivery unit 20 may comprise a pressure sensor 36 for measuring the gas pressure flowing along the conduit 26 and an inspiration branch 28 towards the reciprocating unit 23.

The expiration circuit 22 comprises an expiration valve 37 for discharging the expiration gas and a flow sensor 38, which is optional, for measuring the flow discharged through the expiration valve 37. The expiration circuit is in flow connection along an expiration branch 39 with the reciprocating unit 23 and the manual ventilation circuit 18.

The manual ventilation circuit 18 comprises a manual bag 40 for providing a gas flow such as drive gas flow to increase a pressure needed for the subject inspiration and for receiving the gas flow for the expiration when the subject is expiring, a bag valve 42 for connecting and disconnecting the drive gas flow between the manual bag 40 and the expiration branch 39 or the breathing circuit 16, a sensor 44 such as a flow sensor for detecting a flow direction inside the manual ventilation circuit 18 and a pressure sensor 46 for measuring a pressure of the manual ventilation circuit 18. The drive gas flow to and from the manual bag 40 is arranged through a bag branch 48 and which flow can be detected by the sensor 44 based on which a signal can be produced and which signal can be received by control unit 21 for determining the flow direction and based on which the control unit 21 is able to guide a discharge of extra gas volume. The manual bag 40 can be filled due to the expiration gas flow. It can be filled with the drive gas used when guiding the inspiration. Typically during the expiration the manual bag 40 is filled at least partly with the gas used when guiding the gas from the manual bag to assist the inspiration preceding the present expiration making possible a direct pneumatic contact between the expiration gas flow coming from the lungs of the subject and the manual bag. Also during expiration the manual bag (40) may be filled partly with the gas used when guiding the gas from the manual bag to assist the inspiration and to be filled partly with one of the fresh gas supplied by the gas mixer 27 and the gas flow delivered by the inspiration delivery unit 20.

The gas mixer 27 is arranged to supply the fresh gas through a fresh gas outlet 50 to the breathing circuit 16 for the subject breathing. Typically the fresh gas comprises of oxygen and air or nitrous oxide. Oxygen is delivered through an oxygen delivery line 51 comprising of a filter 52, a pressure regulator 54, an oxygen flow sensor 56 and an oxygen flow control valve 58. The air is delivered through an air delivery line 61 comprising of filter 62, a pressure regulator 64, an air flow sensor 66, and air flow control valve 68. For a delivery of nitrous oxide respective components may be provided (not shown). After metering the individual gas flows, they are merged together for fresh gas mixture delivered to a vaporizer 70 which completes the fresh gas mixture with a volatile anesthesia agent vapor before delivery to the breathing circuit 16 at the fresh gas outlet 50 and to the subject breathing.

The breathing circuit 16, which is operably connected to the machine ventilator circuit 14 at a breathing circuit connection 71 and to the fresh gas outlet 50, comprises an inspiration limb 72 for an inspired gas, an expiration limb 74 for an exhaled gas, a carbon dioxide ($CO_2$) remover 76 such as $CO_2$ absorber to remove or absorb carbon dioxide from the exhaled gas coming from the subject 12, a first one-way valve 78 for an inspired gas to allow an inspiration through the inspiration limb 72, a second one-way valve 80 for an expired gas to allow an expiration through the expiration limb 74, a branching unit 82 such as a Y-piece having at least three limbs, one of them being for the inspired gas, a second one being for the expired gas and a third one being for both the inspired and expired gases and being connectable to by means of the patient limb 84 to the lungs of the subject 12. Also the breathing circuit may comprise a pressure sensor 85 for measuring a pressure of the breathing circuit 16.

In mechanical ventilation the manual bag valve 42 is maintained closed. During the inspiration phase of the machine ventilation the expiration circuit 22 of the machine ventilator circuit 14 closes the expiration valve 37 under the control of the control unit 21. This guides the inspiration gas flow from the inspiration delivery unit 20 through the inspiration branch 28 of a gas branching connector 86 and through the connection 88 of the reciprocating unit 23 pushing the breathing gas out from the breathing circuit connection 71 to the breathing circuit 16. The inspiration gas delivery unit 20 controlled by the control unit 21 delivers the gas flow either to reach the given gas volume or a pressure at subject lungs. For this control the flow sensor 32 for measuring the inspiration flow and the pressure sensor 85 of the breathing circuit 16 are used. Also the volume delivered from the fresh gas mixer 27 is taken into consideration in the delivery of the gas volume.

The first one-way valve 78 for the inspired gas and the second one-way valve 80 for the expired gas of the breathing circuit 16 guide the gas flow direction in the circuit. The inspiration flow is guided through the carbon dioxide remover 76 to remove or absorb from the expiration gas carbon dioxide and further the carbon dioxide free gas is guided through the first one-way valve 78 for an inspired gas to the inspiration limb 72 where it is mixed with the fresh gas flow and therefrom through the branching unit 82 to the patient limb 84 and finally to the lungs of the subject 12.

At the end of the inspiration phase the breathing circuit 16 and the subject lungs are pressurized. For the expiration under the control of the control unit 21 the inspiration delivery flow control valve 34 is closed stopping the inspiration delivery and the expiration valve 37 is opened to allow the gas release from the expiration branch 39 of the drive gas branching connector 86 and further through the connection 88 from the reciprocating unit 23. This allows the pressure release and breathing gas flow from breathing circuit 16 and the lungs of the subject 12 to the reciprocating unit 23. The breathing gas flows from the subject 12 through the patient limb 84, the branching unit 82, the expiration limb 74, the second one-way valve 80 for the expired gas and the breathing circuit connection 71 to the reciprocating unit 23. The pressure release is controlled for a desired expiration pressure such as a positive end expiration pressure (PEEP) target, which may be set using the user interface 25. For this control the ventilator control 21 uses the breathing circuit pressure measured by the pressure sensor 85 and the expiration valve 37. The expiration gas flow may be measured using the flow sensor 38 located in this embodiment at the expiration branch 39 or at the outlet the expiration valve 37 as shown in FIG. 1.

For the manual ventilation the bag valve 42 is opened. Preferably, the bag valve 42 may be electrically or pneumatically actuated. However, that may also have a direct access actuator button or lever for immediate manual access as an alternative. The manual bag valve 42 provides a gas flow path from the expiration branch 39 of the machine ventilator circuit 14 through the sensor 44 for detecting the flow direction inside the manual ventilation circuit 18 and the bag branch 48 to the manual bag 40.

This sensor 44 is utilized to identify the bag operations including the flow to the manual bag 40 and out from the manual bag and to trigger the inspiration and expiration phases of the breath cycle when on the manual ventilation mode. Thus the sensor 44 produces for the control unit 21 a signal to determine the flow direction to guide the expiration circuit 22. As a response to the inspiration triggering, the expiration valve 37 of the expiration circuit 22 is closed to guide the bag compression-induced drive gas flow towards the lungs of the subject.

The operation of the arrangement 10 during the manual ventilation will now be described. The pressure sensor 85 is used to monitor the pressure within the breathing circuit 16. The fresh gas is supplied to the breathing circuit 16 at a required flow rate and the expiration valve 37 is operated by means of the control unit 21 to maintain the given desired expiration pressure in the circuit. The required fresh gas flow rate may be given by the user by means of the user interface 25 or is determined automatically from the required subject gas concentrations. Also the inspiration flow can be used to achieve and maintain the pressure. Because the manual bag 40 is now connected to the breathing circuit 16, the manual bag 40 is also loaded to this same pressure. When the manual inspiration is required, the manual bag 40 is squeezed, causing the pressure within the bag to rise over the desired expiration pressure. The bag squeeze induces the gas flow out from the manual bag 40. This flow direction is detected and determined and the flow is measured with the sensor 44. During the manual ventilation this flow corresponds with the inspiration delivery flow of the mechanical ventilation. The control unit 21 identifies the flow out from the manual bag 40 during the manual inspiration mode meaning that an inspiration phase is active and triggers the ventilation control to the inspiration state. At this state the expiration valve 37 is closed guiding the drive gas from the manual bag 40 towards the reciprocating unit 23, which forces the breathing gas from the breathing circuit connection 71 to the breathing circuit 16 and further through the inspiration limb 72 to the lungs of the subject 12. During the inspiration the expiration valve 37 is maintained closed. However, for safety purposes the lungs must be protected for excessive pressure. Therefore the expiration circuit 22 may be programmed to open the expiration valve 37 in case the measured patient pressure increases beyond the given maximum pressure limit and thus limit the inspiratory pressure.

The inspiration turns to the expiration phase when the manual bag 40 is released. The control unit 21 identifies that the expiration phase is active as the reduced manual bag pressure below the breathing circuit pressure initiates the gas flow from the expiration branch 39 towards the manual bag 40 when the sensor 44 is able to determine the flow direction inside the manual ventilation circuit 18. This triggers the expiration control of the manual breath cycle. This flow can be measured with this sensor 44. As a safety against the sustained pressure, the expiration phase may also be initiated if the inspiration duration exceeds the preset inspiration maximum time or the breathing circuit pressure measured with the pressure sensor 85 exceeds the preset maximum pressure safety limit. Both preset values may be entered using the user interface 25.

During the expiration phase, the breathing gas flows out from the lungs of the subject 12 through the patient limb 84, the branching unit 82, the expiration limb 74, second one-way valve 80 for the expired gas and the breathing circuit connection 71 of the reciprocating unit to the reciprocating unit 23. This forces the drive gas out from the connection 88 of the reciprocating unit to the gas branching connector 86 and further to the expiration branch 39. Because at the beginning of the expiration, when the expiration phase is active, the bag pressure is low, the expiration valve 37 guided by the control unit 21 remains in closed position and the gas flow continues towards the manual bag 40 filling the bag. This gas from the subject lungs to the manual bag 40 at the early expiration phase gives the haptic feedback of the subject exhaled volume. The fresh gas flow and inspiration flow continues the manual bag filling until the bag pressure achieves the desired expiration pressure such as the target PEEP. For this purpose the manual bag 40 is equipped with the pressure sensor 46. Alternatively, the pressure measured with the pressure sensor 36 may be used for the purpose. When the bag pressure reaches the desired expiration pressure, the control unit 21 guides during the expiration mode the expiration valve 37 to an open position to allow the extra gas flow out in order to maintain the desired predetermined pressure measured with the pressure sensor 85 until the next inspiration is detected.

The subject expiration may, however, not give enough volume to fill the manual bag 40 to the desired expiration pressure. This is because during the manual ventilation the breathing circuit 16 is often leaking. Therefore the fresh gas flow and inspiration flow are adjusted to provide a complementary volume to resume the desired expiration pressure after the inspiration. The fresh gas flow rate may be adjusted for the purpose automatically by means of the control unit 21 or the clinician may prefer to select the constant flow rate large enough to reach the target. After reaching the target the control unit 21 guides to maintain the pressure at the target using the expiration valve 37.

During the manual ventilation the subject may also take spontaneous breaths. Typically this happens during the expiration phase of the breath cycle. If the subject demand exceeds the delivered fresh gas flow rate, the breathing circuit pressure measured by the pressure sensor 85 drops below the desired expiration pressure and the control unit 21 guides to close the expiration valve 37. Further the subject demand promotes the gas flow from the manual bag 40 towards the subject 12, which change in the flow direction is detected with the sensor 44 inside the manual ventilation circuit 18 and the control unit 21 identifies as an inspiration. A forthcoming spontaneous expiration, or bag filling from the fresh gas flow and inspiration flow during the subject's spontaneous inspiration hold period is then respectively detected by the sensor 44 as the flow towards the manual bag 40 and the control unit 21 identifies again the expiration phase.

Figure 2:
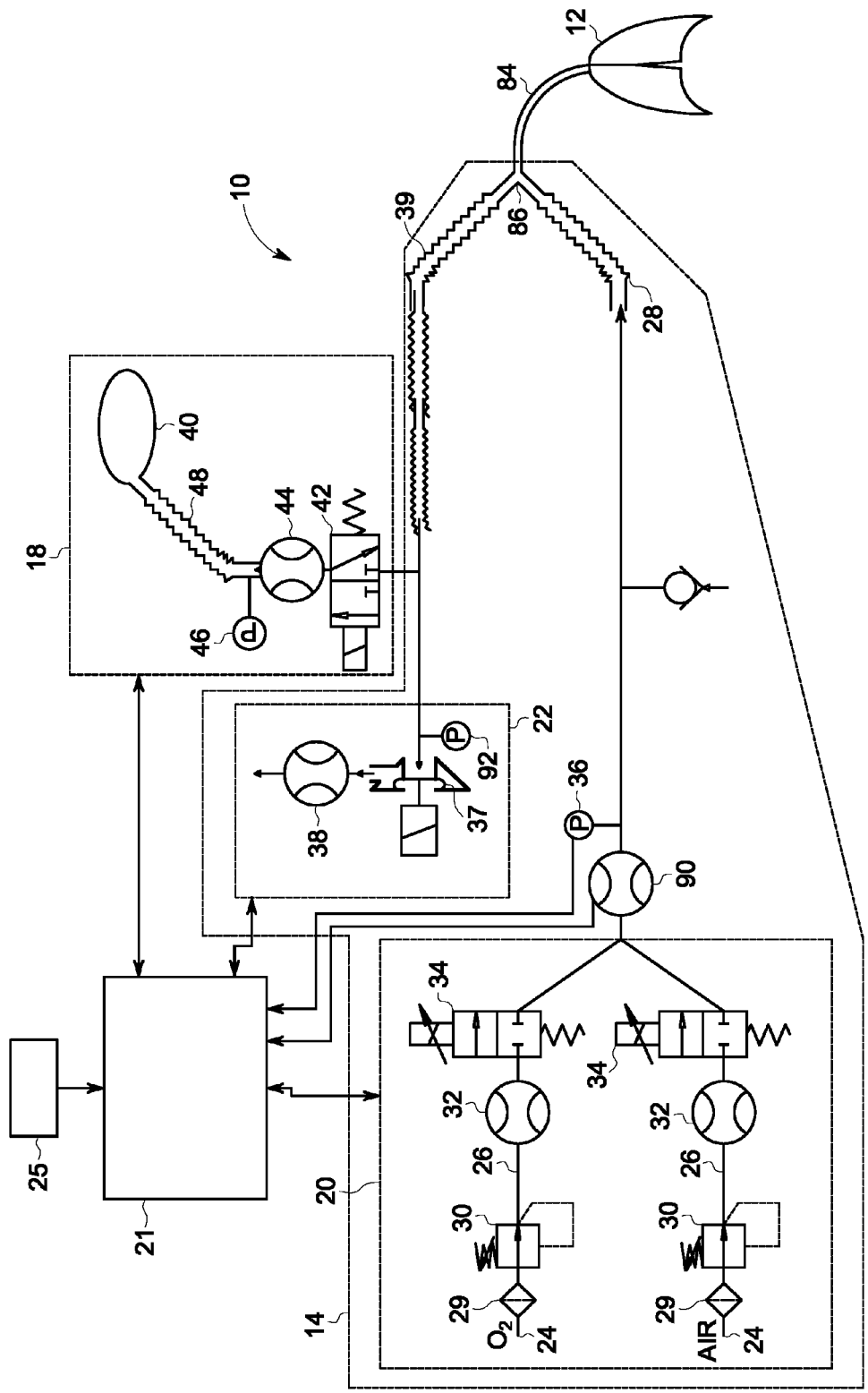
FIG. 2 is an operational diagram of an arrangement for providing an inspiration gas to a subject according to another embodiment.

FIG. 2. shows the arrangement 10 of another embodiment having an open breathing system. Such system neither has separate fresh gas supply nor dedicated drive gas but the drive gas is the mixture of oxygen and air provided directly through its inspiration branch 28, the connection 88, and the patient limb 84 to lungs of the subject 12. In this setting the inspiration delivery unit 20 of the machine ventilator circuit 14 comprises two separate conduits 26 for the gas such as the drive gas. One of those conduits may be for oxygen and another one may be for the air. Both conduits 26 comprises the compressed gas interfaces 24 for inspiration delivery connected to compressed gas supplies (not shown), the filter 29, the pressure regulators 30, the flow sensors 32 for measuring the inspiration delivery flow and the flow control valves 34. These components have been introduced hereinbefore when explaining the FIG. 1 embodiment. After metering the individual gas flows to produce the required gas mixture having the desired $O_2$ concentration and desired total flow rate the gas flows are merged to a gas mixture, which may still be measured for cross referencing the sensor operational condition with total flow sensor 90. Also it is desired to measure the pressure of the merged gas mixture by means of the pressure sensor 36.

In FIG. 2 the expiration circuit 22 of the open breathing system just as the FIG. 1 embodiment also comprises the expiration valve 37 and optionally the flow sensor 38 connected either downstream or upstream to the expiration valve 37. Further in this embodiment the expiration circuit 22 may comprise a pressure sensor 92 for measuring the pressure prevailing in the expiration branch 39. The bag branch 48 of the manual ventilation circuit 18 connects through the bag valve 42 to the expiration branch 39. The manual ventilation circuit 18 is equipped with the sensor 44 for detecting the flow direction inside the manual ventilation circuit 18. Optionally the manual ventilation circuit 18 is also equipped with the pressure sensor 46 just as the embodiment in FIG. 1.

In operation of the manual ventilation with the open breathing circuit as shown in FIG. 2 the inspiration delivery unit 20 provides a gas flow towards the inspiration branch 28 and the connection 88 and the patient limb 84 to pressurize the lungs of the subject 12 and the manual bag 40 to the desired expiration pressure such as a given PEEP pressure. Once that is achieved, the expiration circuit 22 regulates the expiration valve 37 to maintain the desired expiration pressure.

When the manual bag 40 is squeezed the gas flow direction out from the manual bag 40 is detected with the sensor 44. The expiration valve 37 is closed as a response to this and the gas flow deflating from the compressed manual bag 40 flows through the expiration branch 39, the connection 88, and patient limb 84 to the lungs of the subject 12. The inspiration flow delivered through the flow control valves 34 may complete the lung filling or alternatively the gas flow from the inspiration delivery unit 20 may be stopped for the inspiration to give the full haptic feel of the lung filling.

The manual bag release is detected by the sensor 44, when the gas flow direction is changed towards the manual bag 40. During the expiration, after the manual bag pressure reaches the desired expiration pressure level measured with the pressure sensor 46 of the manual ventilation circuit 18 or the pressure sensor 92 of the expiration circuit 22, the expiration valve 37 is regulated by means of the control unit 21 for the desired expiration pressure at the expiration branch 39 measured with the pressure sensor 36 of the inspiration branch 28 or the pressure sensor 92 in flow connection with the expiration branch 39. Filling the manual bag 40 from the subject expiration gives clinician the haptic feedback of subject expiration volume.

The sensor 44 shown in FIGS. 1 and 2 for detecting the flow direction inside the manual ventilation circuit 18 can be of any known type used for detecting the flow direction or sensing flow rate. These include hot wire anemometer, ultrasonic flow sensor or a flow restriction type flow sensor where the differences in pressure generated by the flow rate through the flow restriction is measured. This pressure can be measured with a differential type pressure sensor connected over the flow restriction, or alternatively, the control unit 21 can calculate the pressure difference using the pressures measured with the sensor 44 of the manual ventilation circuit 18, in case the sensor 44 is a pressure sensor comparing the pressure of the manual ventilation circuit 18 and outside pressure prevailing outside the arrangement 10, and some other pressure sensor which may be part of the arrangement 10 and the machine ventilation circuit 14 outside the manual ventilation circuit 18, which is typically the pressure sensor 36 in flow connection with the inspiration branch 28 and measuring the drive gas pressure or the pressure sensor 92 in flow connection with the expiration branch 39 and measuring the expiration gas pressure of the machine ventilator circuit 14. To determine the flow direction the pressure sensor 36 or the pressure sensor 92 as well as the sensor 44 provide a signal to the control unit 21. Examples of usable flow restrictions are an orifice or variable orifice. Even the bag valve 42 can be utilized as a flow restriction.

In connection to the open breathing system as shown in FIG. 2, the manual inspiration is pushing the gas from the expiration branch 39 to the subject. The expiration gas from the subject as well flows through the expiration branch 39. This expiration gas contains carbon dioxide and the oxygen concentration is low. Therefore, advantageous to the manual ventilation of the embodiment is that the expiration branch 39 is filled with the gas from the inspiration delivery unit 20 before the new inspiration. This requires a controlled gas flow from the inspiration delivery unit 20 during the expiration directly through the connection 88 to expiration branch 39 and when the desired expiration pressure is achieved, further through the expiration valve 37 out from the expiration branch 39 or the machine ventilator circuit 14. This by-flow should be at least equal to minute ventilation volume, which is typically for adult subjects 5-6 L/min but can be 10 L/min or even higher if needed. This requires also that the expiration branch 39 accommodates the volume of one inspiration, which is for adult subjects typically 500 mL and less than 1000 mL. With typical 22 mm diameter expiration branch this corresponds to 3 m expiration tube length.

Figure 3:
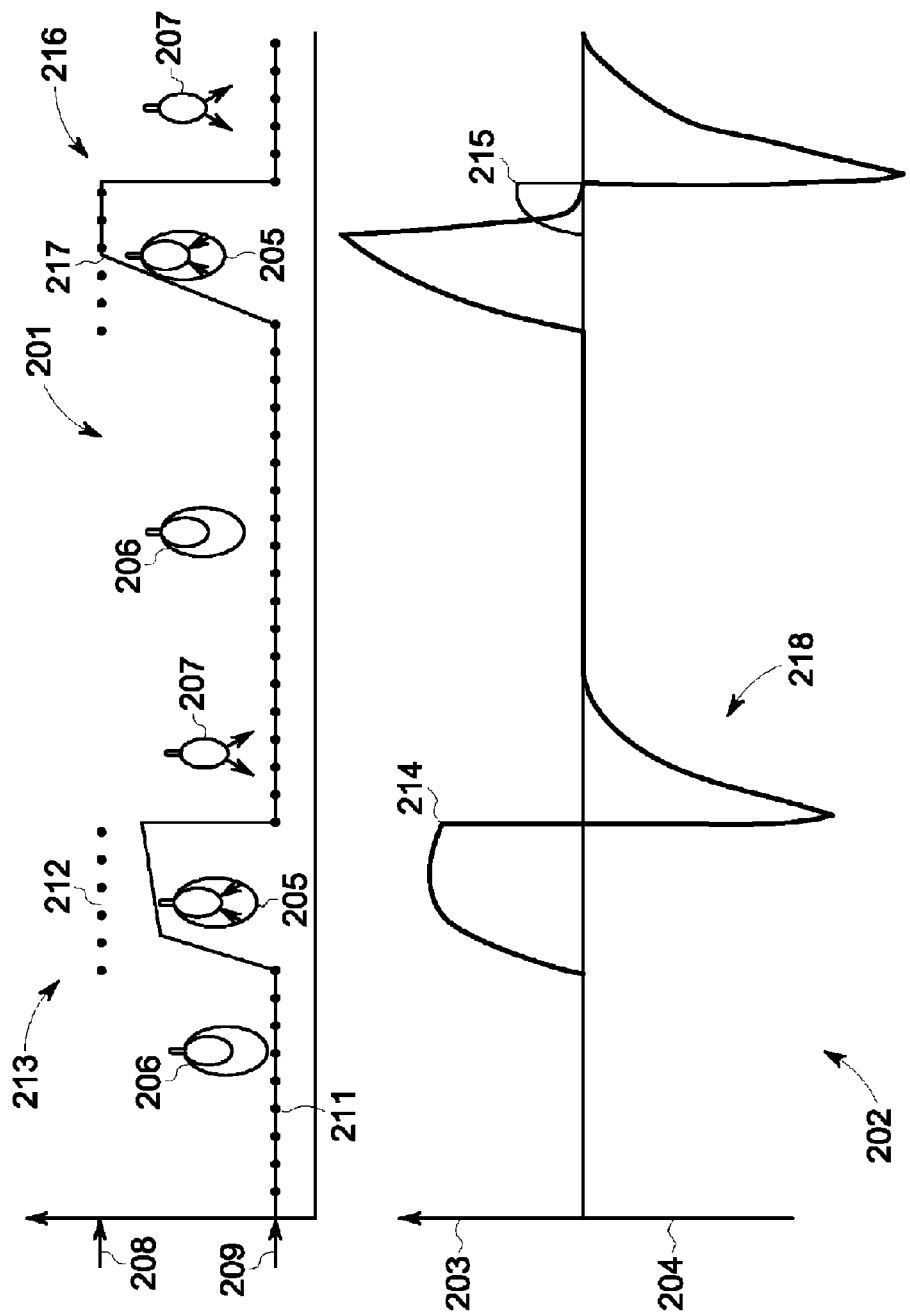
FIG. 3 presents the breathing circuit pressure and subject flow responses when using a manual ventilation.

FIG. 3 describes graphically the pressure and flow time characteristics of the manual ventilation of the embodiment. An ordinate of a graph 201 denotes the manual ventilation pressure on the breathing circuit 211 and an abscissa defining a time. An arrow 208 determines the given maximum breathing circuit pressure and an arrow 209 the desired expiration pressure. A dot line 212 represents a pressure the control unit 21 is working with. A graph 202 ordinate is the respective flow, inspiration on upward direction 203 and expiration down direction 204. The thick line 214 represents the subject flow and a thin line 215 represents the gas flow out from the breathing system. FIG. 3 presents also the manual ventilation phases with symbolic variation of the manual bag size comprising an inspiration 205, expiration 206 and early expiration 207.

At an inspiration phase 213 the manual bag squeeze is gentle and the breathing circuit pressure is not increasing up to the given maximum pressure. At this breath all the gas flow reaches the patient. Following an expiration flow 218 inflates the manual bag 40 giving the feedback of the successful breath. During the expiration the control unit 21 guides to deliver further gas to the breathing circuit to reach the desired expiration pressure and regulates the expiration valve 37 to maintain that throughout the expiration.

At an inspiration phase 216 the bag pressing is more aggressive and the dot line 212 of the maximum pressure limit is achieved at point 217. At this point the further manual bag depression causes increasing gas flow out from the breathing system instead of the subject in order to limit further inspiratory pressure increase.

The advantage of the embodiments is that triggering between the inspiration and expiration phases of the breath cycle using the flow inside the manual ventilation circuit 18 is sensitive and independent of the strength by which the manual bag 40 is compressed. The embodiments provides also a protection for sustained lung pressure and barotrauma during the manual ventilation and provides a user adjustable desired expiration pressure. It also provides haptic feedback on both true inspired and expired gas volumes to the user.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system for ventilating lungs of a subject, the system comprising:
a control unit configured to control operation of the system;
a machine ventilator circuit configured to assist breathing functions of the subject, the machine ventilator circuit comprising an inspiration delivery unit for delivering gas flow along an inspiration branch and an expiration circuit for discharge of an expiration gas along an expiration branch, the expiration circuit comprising an expiration valve; and
a manual ventilation circuit in flow connection with the expiration branch, the manual ventilation circuit comprising:
a manual bag, wherein a first gas flow is guided out from the manual bag to the expiration branch to assist an inspiration phase, a second gas flow is received to fill the manual bag during an expiration phase; and
a first sensor, wherein the first sensor is configured to detect a flow direction inside the manual ventilation circuit and to provide a first signal to the control unit based on the detected flow direction; and
wherein the machine ventilator circuit comprises a second sensor, wherein the second sensor is configured to detect the pressure inside the machine ventilation circuit and to provide a second signal to the control unit based on the pressure inside the machine ventilation circuit;
wherein the control unit controls the inspiration delivery unit and the expiration circuit in response to the first and second signals and is configured to identify whether the inspiration phase or the expiration phase is active and to guide the expiration valve, when the expiration phase is active, to be in a close position allowing the gas flow towards the manual bag filling it until the second signal indicates to the control unit that the pressure of the manual bag achieves a predetermined pressure after which the control unit is configured to guide the expiration valve to an open position to allow extra gas flow out in order to maintain the predetermined pressure.

2. The system according to claim 1, wherein the machine ventilator circuit and the manual ventilation circuit can be alternatively selected.

3. The system according to claim 1 further comprising:
a user interface for entering information while ventilating the subject.

4. The system according to claim 1, wherein direct pneumatic contact is made between the manual bag and the second gas flow received to fill the manual bag during the expiration phase.

5. The system according to claim 1 further comprising:
a gas mixer configured to supply fresh gas to the subject and a breathing circuit connecting lungs of the subject and the machine ventilator circuit to exchange gas in the lungs.

6. The system according to claim 5, wherein the second gas flow received to fill the manual bag during the expiration phase further comprises at least one of the fresh gas supplied by the gas mixer and a gas flow delivered by the inspiration delivery unit, and wherein direct pneumatic contact is made between the manual bag and the gas flow received to fill the manual bag during the expiration phase.

7. The system according to claim 1, wherein the first sensor is a flow sensor.

8. A method for ventilating lungs of a subject with a system comprising a control unit configured to control operation of the system; a machine ventilator circuit configured to assist breathing functions of the subject and comprising an inspiration delivery unit, an expiration circuit for controlling a discharge of expiration gas, wherein the expiration circuit includes an expiration valve, and a pressure sensor configured to detect pressure inside the mechanical ventilation circuit; and a manual ventilation circuit comprising a manual bag and a flow direction sensor, the method comprising:

increasing pressure to guide a first gas flow to assist an inspiration phase during compression of the manual bag;

guiding, with the control unit, a second gas flow that at least partially comprises the gas flow guided to assist the inspiration phase to fill the manual bag during an expiration phase;

detecting a flow direction inside the manual ventilation circuit with the flow direction sensor;

providing a signal to the control unit with the flow direction sensor based on the detected flow direction to indicate the inspiration phase or the expiration phase;

controlling, with the control unit, the inspiration delivery unit, the expiration circuit and the expiration valve of the system in response to the signal; and guiding, with the control unit, a discharge of extra gas volume based on the detected flow direction, when the expiration phase is active, such that the expiration valve is in a closed position allowing gas to flow towards the manual bag filling it at least partly with the extra gas volume if the pressure sensor has not indicated to the control unit that the pressure of the manual bag has achieved a predetermined pressure after which the expiration valve is in an open position to allow the extra gas volume out in order to maintain the predetermined pressure, wherein the extra gas volume is discharged during the expiration phase in order to reach a pressure level of an expiratory pressure.

9. The method according to claim 8 further comprising setting a predetermined pressure level for the expiratory pressure and setting a predetermined pressure level for limiting an inspiratory pressure.

10. The method according to claim 8, wherein filling the manual bag during the expiration phase with a gas flow that at least partially comprises the gas flow guided to assist the inspiration phase creates direct pneumatic contact between the manual bag and the gas flow received to fill the manual bag during the expiration phase.

11. The method according to claim 8, further comprising supplying a gas flow of fresh gas to the subject.

12. The method according to claim 11, wherein filling the manual bag during an expiration phase further comprises the gas flow of fresh gas.

13. The method according to claim 8, wherein the machine ventilator circuit and the manual ventilation circuit can be alternatively selected.

14. The method according to claim 13, wherein the manual ventilation circuit is in gas flow connection with at least a part of the machine ventilator circuit to create a pneumatic contact with the lungs of the subject when the manual ventilation circuit is selected, and the manual ventilation circuit being in gas flow connection with an expiration circuit to achieve a predetermined pressure level under the control of the control unit, the method further comprises:

increasing pressure by compressing the manual bag to guide a gas flow to assist an inspiration phase in the manual ventilation circuit and in a part of the machine ventilator circuit in flow communication with the manual ventilation circuit; and releasing the manual bag for an expiration phase.

15. The method according to claim 14, further comprising setting a predetermined pressure level for the expiratory pressure and setting a predetermined pressure level for limiting an inspiratory pressure.

16. The method according to claim 14, wherein filling the manual bag during the expiration phase with a gas flow that at least partially comprises the gas flow guided to assist the inspiration phase creates direct pneumatic contact between the manual bag and the gas flow received to fill the manual bag during the expiration phase.

* * * * *